United States Patent [19]
Rydel et al.

[11] Patent Number: 5,866,318
[45] Date of Patent: Feb. 2, 1999

[54] INHIBITION OF PHOSPHOLIPASE A$_2$ TO REDUCE NEURONAL CELL DEATH

[75] Inventors: Russell E. Rydel, Belmont; Michael S. Dappen, San Bruno, both of Calif.

[73] Assignee: Athena Neurosciences, Inc., South San Francisco, Calif.

[21] Appl. No.: 476,463

[22] Filed: Jun. 7, 1995

[51] Int. Cl.$^6$ .............................. C12Q 1/00; C12Q 1/68; C12N 5/06

[52] U.S. Cl. ................................. 435/4; 435/6; 435/325; 435/375; 435/377

[58] Field of Search .................................. 435/29, 240.2, 435/69.1, 4, 6, 7.21, 3.25, 3.75, 3.77; 514/603

[56] References Cited

U.S. PATENT DOCUMENTS

| | | | |
|---|---|---|---|
| 5,137,873 | 8/1992 | Yankner | 514/15 |
| 5,276,059 | 1/1994 | Caughey et al. | 514/647 |
| 5,281,626 | 1/1994 | Oinuma et al. | 514/603 |
| 5,328,842 | 7/1994 | Chiou et al. | 435/352 |
| 5,354,677 | 10/1994 | Knopf et al. | 435/198 |
| 5,453,443 | 9/1995 | Perrier et al. | 514/570 |
| 5,478,857 | 12/1995 | Clemens et al. | 514/381 |

FOREIGN PATENT DOCUMENTS 0 468 054 A1  1/1992  European Pat. Off. .

OTHER PUBLICATIONS

Agarwal et al "Phospholipase Activation Triggers Apoptosis is Photosenstized Mouse lymphoma Cells"Cancer Research vol. 53:5897–5902, Dec. 15, 1993.

Lockhart et al. "Inhibitors of Free Radical Formation Fail to Attenuate Direct beta–Amyloid25–35 Peptide–Mediated Neurotoxicity in Rat Hippocampal Cultures", Journal of Neuroscience Research, vol. 39, No. 4, pp. 495–505, 1994.

Sipe "Amyloidosis", Annual Review of Biochemistry, vol. 61, pp. 947–975, 1992.

Eikelenboom, Piet et al., Inflammatory mechanisms in Alzheimer's disease, *Tips*, vol. 15, Dec. 1994.

Simmons, Linda K., et al., "Secondary Structure of Amyloid β Peptide Correlates with Neurotoxic Activity in Virto," *The American Society for Pharmacology and Experimental Therapeutics*, Molecular Pharmacology, 45:373–379, Mar. 1994.

Dumuis, Aline, et al., *Stimulation by Glutamate Receptors of Arachidonic Acid Release Depends on the $Na^+/Ca^{2+}$ Exchanger in Neuronal Cells, The American Society for Pharmacology and Experimental Therapeutics*, Molecular Pharmacology, 43:976–981, Jun. 1993.

Alberts, Bruce, et al., Molecular Biology of The Cell, Second Edition, 1989.

Abdullah et al., "Human cytosolic phospholipase A$_2$ expressed in insect cells is extensively phosphorylated on Ser–505," *Biochimica et Biophysica Acta*, 1244:157–164 (1995).

Abdullah et al., "Synthesis and Preparation of an Affinity Chromatography Column for the Purification of Cytosolic Phospholipase A$_2$," *Bioorganic & Medicinal Chemistry Letters*, 5(5):519–522 (1995).

Abdullah et al., "Purification of Baculovirus–Overexpressed Cytosolic Phospholipase A$^2$ Using a Single–Step Affinity Column Chromatography," *Protein Expression and Purification*, 6:291–297 (1995).

Ackermann et al., "Inhibition of Macrophage $Ca^{2+}$–independent Phospholipase A$_2$ by Bromoenol Lactone and Trifluoromethyl Ketones," *J. Biol. Chem.*, 270 (1):445–450 (1995).

Bartoli et al., "Tight Binding Inhibitors of 85–kDa Phospholipase A$_2$ but Not 14–kDa Phospholipase A$_2$ Inhibit Release of Free Arachidonate in Thrombin–stimulated Human Platelets," *J. Biol. Chem.*, 269(22):15625–15630 (1994).

Currie et al., "Phosphorylation and activation of $Ca^{2+}$–sensitive cytosolic phospholipase A$_2$ MCII mast cells mediated by high–affinity $F_c$ receptor for IgE," *Biochem. J.*, 304:1–6 (1994).

Dennis, "Diversity of Group Types, Regulation, and Function of Phospholipase A$_2$," *J. Biol. Chem.*, 269(18):10357–13060 (1994).

Glaser et al., "Phospholipase A$_2$ enzymes: regulation and inhibition," *TiPS*, 14:92–98 (1993).

Kramer, "Structure, Function and Regulation of Mammalian Phospholipases A$_2$ ,"*Advances in Second Messenger and Phosphoprotein Research*, 28:81–89 (1993).

Lin et al., "cPLA$_2$ Is Phosphorylated and Activated by MAP Kinase," *Cell*, 72:269–278 (1993).

Mattson et al., "β–Amyloid precursor protein metabolites and loss of neuronal $Ca^{2+}$ homeostasis in Alzheimer's disease," *TINS*, 16(10):409–414 (1993).

Meda et al., "Activation of microglial cells by β–amyloid protein and interferon–τ," *Nature*, 374:647–650 (1995).

Oinuma et al., "Synthesis and Biological Evaluation of Substituted Benzenesulfonamides as Novel Potent Membrane–Bound Phospholipase A$_2$ Inhibitors," *J. Med. Chem.*, 34:;2260–2267 (1991).

Petit et al., "Isolation and Characterization of a Cytosolic Phospholipase A$_2$ from Bovine Adrenal Medulla," *J. of Neurochem.* 64:139–146 (1995).

(List continued on next page.)

*Primary Examiner*—George C. Elliott
*Assistant Examiner*—Sean McGarry
*Attorney, Agent, or Firm*—Townsend and Townsend and Crew, LLP

[57] ABSTRACT

The invention is drawn to a method for identifying agents that inhibit neural degeneration by administering to cell populations consisting essentially of neurons or cells from neuronal cell lines, where these cells are exposed to an apoptotic stimulus other than APP gene products, an agent, where it is determined whether the agent inhibits neural degeneration.

12 Claims, 4 Drawing Sheets

OTHER PUBLICATIONS

Reynolds et al., "1–Hexadecyl–2–Archidonoylthio–2–deoxy–sn–Glycero–3–Phosphorylcholine as a Substrate for Microtiterplate Assay of Human Cytosolic Phospholipase $A_2$," *Anal. Biochem.*, 217:25–32 (1994).

Reynolds et al, "Assay Strategies and Methods for Phospholipases," *Methods in Enzymology*, 197:3–23 1991).

Riendeau et al., "Arachidonyl Trifluoromethyl Ketone, a Potent Inhibitor of 85–kDa Phospholipase $A_2$, Blocks Production of Arachidonate and 12–Hydroxyeicosa–tetraenoic Acid by Calcium Ionophore–challenged Platelets," *J. Biol. Chem.*, 269(22):15619–15624 (1994).

Roshak et al., "Suppression of Monocyte 85–kDa Phospholipase $A_2$ by Antisense and Effects on Endotoxin–induced Prostaglandin Biosynthesis," *J. Biol. Chem.*, 269(42):25999–26005 (1994).

Street et al., "Slow–and Tight–Binding Inhibitors of the 85–kDa Human Phospholipase $A_2$," *Biochem.*, 32:5935–5940 (1993).

Verity, "Mechanisms of Phospholipase $A_2$ Activation and Neuronal Injury," *Annals NY Acad. Sci.*, 379:110–120 (1993).

QUINACRINE

MINOCYCLINE
FIG. 3F.

MANOALIDE
FIG. 3G.

AN22669
FIG. 3H.

OLEOYLOXYETHYL PHOSPHOCHOLINE
FIG. 3I.

p-BROMOPHENACYL BROMIDE
FIG. 3J.

7,7-DIMETHYLEICOSADIENOIC ACID
FIG. 3K.

DOXYCYCLINE
FIG. 3L.

AN23019
FIG. 3M.

INHIBITION OF PHOSPHOLIPASE A₂ TO REDUCE NEURONAL CELL DEATH

TECHNICAL FIELD

The invention relates to methods for inhibiting cell death in mammalian cells, particularly in neuronal cells, by administering a suitable inhibitor of phospholipase $A_2$ activity, typically an inhibitor of $cPLA_2$ (cytosolic phospholipase $A_2$); the invention also provides methods for identifying such suitable inhibitors of phospholipase activity, including selective inhibitors of $PLA_2$, which have the property of inhibiting cell death and neuronal degeneration in response to a variety of toxic effectors and apoptotic stimulants.

BACKGROUND

Cell death is an important aspect during the embryonic or post-natal development of major organ systems. Apoptosis, or programmed cell death, also plays a critical role in maintaining homeostasis in many adult tissues. Apoptosis is a term used to refer to the process(es) of programmed cell death and has been described in several cell types (Waring et al. (1991) *Med. Res. Rev.* 11: 219; Williams GT (1991) *Cell* 65: 1097; Williams GT (1992) *Trends Cell Biol.* 2: 263; Yonisch-Rouach et al. (1991) *Nature* 352: 345). Apoptosis is likely involved in controlling the amount and distribution of certain differentiated cell types, such as lymphocytes and other cells of the hematopoietic lineage as well as other somatic and germ cells. The mechanism(s) by which apoptosis is produced in cells is incompletely understood, as are the regulatory pathways by which the induction of apoptosis occurs.

Apoptosis Mechanism(s)

Apoptosis was first described as a morphologic pattern of cell death characterized by cell shrinkage, membrane blebbing and chromatin condensation culminating in cell fragmentation (Kerr et al., 1972). One hallmark pattern early in the process of cell death is internucleosomal DNA cleavage (Wyllie, 1980). The death-sparing effects of interrupting RNA and protein synthesis and the stereotyped patterns of cell death during development were consistent with a cell autonomous genetic program for cell death (Wyllie et al. (1980) *Int. Rev. Cytol.* 68: 251; Sulston, J. and Horvitz, H. (1977) *Develop. Biol.* 56: 110; Abrams et al. (1993) *Development* 117: 29). The isolation of mutants defective for developmental cell death in the nematode Caenorhabditis elegans supported this view (Ellis, H. and Horvitz, H. (1986) *Cell* 44: 817; Hengartner et al. (1992) *Nature* 356: 494). Control of apoptosis may be a regulatory feature of a variety of diseases, such as aging, AIDS, and autoimmune diseases, among others. Despite the identification of genes necessary for cell death and the ability to regulate apoptosis by known genes, the essential biochemical events in apoptotic death remain largely unknown.

Cell Proliferation Control and Neoplasia

Many pathological conditions result, at least in part, from aberrant control of cell proliferation, differentiation, and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes. Despite progress in developing a more defined model of the molecular mechanisms underlying the transformed phenotype and neoplasia, few significant therapeutic methods applicable to treating cancer beyond conventional chemotherapy have resulted.

Thus, it is desirable to identify agents which can modify apoptosis activity so as to modulate cell proliferation, differentiation, and/or apoptosis for therapeutic or prophylactic benefit. Further, such agents can serve as commercial research reagents for control of cell proliferation, differentiation, and/or apoptosis in experimental applications, and/or for controlled proliferation and differentiation of predetermined stem cell populations in vitro, in ex vivo therapy, or in vivo.

A variety of neurodegenerative diseases are characterized by cell death of neurons by a mechanism that is not presently distinguishable from many known models of apoptosis. Some of these neurodegenerative diseases appear to be related to excess accumulation of certain proteins. Examples of such amyloidosis-related neurodegenerative diseases include those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy), among others. Although much current effort is being expended on certain neuronal diseases associated with senile dementia, there is less effort being devoted to neurodegenerative diseases which are related to excess accumulation of certain proteins other than the Aβ peptide.

It would be desirable to have compounds and methods or treating non-Alzheimer's type neurodegenerative diseases wherein neuron loss is produced by apoptotic cell death which can be circumvented by suitable therapeutic intervention with pharmaceuticals.

There is a need in the art for pharmaceuticals which have therapeutic use to treat or prevent such apoptosis-related neurodegenerative diseases which have similar pathogenic mechanisms. A more thorough understanding of the molecular events underlying the development and progression of such neurodegenerative diseases would facilitate development of such pharmaceuticals. Identification of critical biochemical events involved in these apoptosis-related neurodegenerative diseases can provide a basis for development of methods and model systems for screening compound banks to identify such pharmaceuticals, as well as providing a basis for the design of therapeutic methods and treatment modalities for neurodegenerative disease.

It would be desirable to have methods and model systems for screening test compounds for the ability to inhibit or prevent or inhibit neuronal toxicity produced by neurotoxic agents which induce neuronal apoptosis. In particular, it would be desirable to base such methods and systems on metabolic pathways and/or signal transduction pathways which have been found to be involved in such pathogenesis, where the test compound would be able to interrupt or interfere with the metabolic pathway or signal transduction pathway which leads to damage of neuronal and/or glial cells in the presence of a pathogenic apoptotic stimulus. Such methods and systems should provide rapid, economical, and suitable means for screening large numbers of test compounds.

Based on the foregoing, it is clear that a need exists for identification of metabolic pathways and/or signal transduction pathways which have been found to be involved in the pathogenesis of apoptosis-related neurodegenerative diseases, and the development of methods of treatment and pharmaceutical screening assays based on the identification of these pathways. The present invention fulfills these and other needs in the art.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

A basis of the present invention is the unexpected finding that apoptosis-mediated neuronal cell degeneration is mediated by a biochemical cascade which requires activity of phospholipase $A_2$, ("$PLA_2$"), an enzyme which catalyzes the hydrolysis of the fatty acid ester bond at the sn-2 position of membrane phospholipids to produce arachidonic acid and its metabolites, and in the case of one cytosolic form of $PLA_2$, $cPLA_2$, also produces lysophospholipids. Agents which selectively block $PLA_2$ activity in neurons and/or glial cells and/or astrocytes or monocytes can be used to inhibit neuronal degeneration, such as that which results from exposure of such cells to pathogenic apoptotic stimuli as occurs in mellitin neurotoxicity and other neurodegenerative conditions. These selective $PLA_2$-blocking agents can be used to inhibit neuronal degeneration resulting from neuronal apoptosis.

In one aspect, the invention provides a method for identifying active agents which significantly inhibit neuronal degeneration induced by pathogenic apoptotic stimuli, either directly or via their effects on secondary cell types such as glial cells, astrocytes, macrophages, or other non-neuronal cells which interact with central nervous system neurons and which can manifest toxicity. The method comprises administering an agent to a cell population comprising neurons, wherein said cell population is exposed to an amount of pathogenic apoptotic stimulus capable of inducing neuronal degeneration in the cell population, and determining whether the presence of said agent produces inhibition of $PLA_2$ activity and, typically, also produces a detectable reduction in the amount and/or rate of neuronal degeneration in the cell population; if said agent produces $PLA_2$ inhibition in neurons and/or inhibits neuronal degeneration, the agent is thereby identified as an active agent. Preferably, the method is used to demonstrate that the active agent inhibits $PLA_2$ activity and also inhibits neuronal degeneration subsequent to a known apoptotic stimulus (e.g., NGF withdrawal or serum withdrawal).

In a variation of the method, the agent is initially selected from a bank (or library) of compounds on the basis of the agent's capacity or selectivity for inhibiting $PLA_2$ in vitro, such as by its ability to inhibit $PLA_2$ enzymatic activity in an in vitro assay employing a predetermined amount of a standardized preparation of $PLA_2$; an agent which is thus initially selected is administered to a cell population comprising neurons, wherein said cell population is exposed to an amount of pathogenic apoptotic stimulus (e.g., NGF withdrawal or serum withdrawal) capable of inducing neuronal degeneration in the cell population, and the capacity of said agent to produce a detectable reduction in the amount and/or rate of neuronal degeneration in the cell population is determined, with agents capable of reducing neuronal degeneration being thereby identified as active agents. In this variation, the capacity of the agent to selectively or specifically inhibit $PLA_2$ in a cultured cell population comprising neurons can optionally be determined.

In an aspect, the invention also provides a method for identifying an active agent which significantly inhibits neuronal degeneration in a transgenic animal model of neuronal apoptosis; such active agents can be sold commercially as reagents to control the disease phenotype of such transgenic animals for any purpose desired by an end-user of such animals, and can serve as candidate pharmaceuticals for therapy of neurodegenerative disease, among other uses. The method comprises initially selecting an $PLA_2$-inhibiting agent from a bank (or library) of compounds on the basis of: (1) the agent's capacity, selectivity, or specificity for inhibiting $PLA_2$ in vitro, such as by its ability to inhibit $PLA_2$ enzymatic activity in an in vitro assay employing a predetermined amount of a standardized preparation of $PLA_2$, and/or (2) the capacity of the agent to selectively inhibit $PLA_2$ in a cultured cell population comprising neurons; and administering the selected agent to a transgenic animal capable of developing detectable pathology characteristic of a neurodegenerative disease, and determining whether administration of the selected agent inhibits or retards development of said detectable pathology as compared to a substantially identical identifying control transgenic animal which lacks the agent; an agent which retards or inhibits development of neuropathology is thereby identified as an active agent.

In an aspect, the invention provides a method for reducing or retarding neurodegeneration in a cell population comprising neurons and exposed to an amount of a pathogenic apoptotic stimulus sufficient to produce neurodegeneration; said method comprising administering an efficacious dose of a $PLA_2$ inhibitor predetermined to retard or inhibit neuronal degeneration. In one embodiment, the cell population may reside in the central nervous system of a mammal and the $PLA_2$ inhibitor is administered in vivo. The invention also provides the use of a $PLA_2$ inhibitor to treat neurodegenerative disease pathology in a mammal.

In an aspect, the invention provides a method for retarding or inhibiting neurodegeneration in a cell population comprising neurons and exposed to an amount of pathogenic apoptotic stimulus sufficient to produce neurodegeneration; said method comprising administering to the cell population an efficacious dose of an antisense polynucleotide capable of inhibiting expression of $PLA_2$, typically by reducing transcription and/or translation of the $PLA_2$ gene sequences. In one embodiment, the cell population may reside in the central nervous system of a mammal and the $PLA_2$ inhibitor is administered in vivo. The invention also provides the use of a $PLA_2$ antisense polynucleotide to treat neurodegenerative disease pathology in a mammal; the neurodegenerative disease resulting from an apototic stimulus other than $A\beta$ peptide. In an embodiment, the antisense polynucleotide is produced by transcription of a transgene or gene therapy vector incorporated into a cell or animal; alternatively, antisense oligonucleotides can be administered in soluble form, formulated in liposomes, or by other suitable delivery format.

In an aspect, the invention provides a transgenic animal, such as a transgenic mouse, which harbors a transgene encoding a functional $PLA_2$ enzyme and capable of transcription and translation in neuronal and/or astrocytes and/or glial cells in vivo. Typically, the transgene comprises a gene encoding a human $PLA_2$ enzyme operably linked to a transcriptional regulatory sequence which is transcriptionally active in neural cell types, and is preferably inducible. In one variation, the 5' flanking portion of the murine or human $PLA_2$ or brain-specific gene, including the promoter (and frequently including an upstream portion and/or intronic portion(s) often having enhancer activity) and sufficient to drive transcription of linked sequences in the brain of a transgenic animal, serves as the transcriptional regulatory sequence of the PLA$_2$-encoding transgene. Such transgenic animals can overexpress PLA$_2$, either constitutively or inducibly, and can serve as models of accelerated neurodegenerative disease; such animals can be sold for toxicological and pharmaceutical applications for evaluation of compounds or agents (physical or chemical) which modulate PLA$_2$-mediated apoptotic neurodegeneration.

The invention also provides, in an aspect, a knockout animal comprising a genome having a homozygous pair of functionally disrupted endogenous PLA$_2$ alleles, such that substantially no endogenous PLA$_2$ is expressed. In a variation, the knockout animal genome also comprises a transgene encoding a heterologous PLA$_2$ enzyme (e.g., a PLA$_2$ knockout mouse having a transgene encoding human PLA$_2$), which is expressed under the control of an operably linked transcriptional regulatory sequence, such as the naturally occurring mouse PLA$_2$ promoter and 5' flanking sequence.

In a variation, the invention provides a knockout mouse having a genome comprising a homologous pair of functionally inactivated mouse PLA$_2$ alleles and a transgene encoding and expressing a pathogenic neurotoxic gene product, such as a prion protein (PrP), mellitin, or the like. Optionally, the mouse genome may further comprise a transgene encoding a mammalian PLA$_2$ which is transcribed under the control of a transcriptional regulatory sequence which is inducible or repressible in neuronal cells.

Optionally, a naturally-occurring mouse model of neurological disease (e.g., Shaker and the like) can be employed.

In an aspect of the invention, an agent is selected from a compound library on the basis of its detectable inhibition of PLA$_2$ activity in an in vitro PLA$_2$ enzyme assay and/or in a cell culture PLA$_2$ assay system; the agent is administered to a transgenic animal of the invention which is expressing PLA$_2$ in neuronal tissue to thereby generate a treated transgenic animal refractory to neurodegenerative pathology and/or evaluate the suitability of the selected agent for in vivo administration.

Also provided by the invention is a method for inhibition of neuronal cell death in a cell population comprising mammalian glial cells and neuronal cells. The method comprises delivering an effective dosage of an PLA$_2$ inhibitor to a cell population comprising neurons which are exposed to an apoptotic stimulus or neurotoxicity. Typically, the cell population is a co-cultured cell population of rat or human cortical or hippocampal neurons and human microglia and/or human astrocytes and/or monocytes. In some variations, transgenic animals may serve as the source of the glial and/or neuronal cells. The cell population also may reside in a mammalian central nervous system in vivo.

Other aspects of the invention will be evident by reference to the specification and examples provided herein.

All publications and patent applications herein are incorporated by reference to the same extent as if each individual publication or patent application was specifically and individually indicated to be incorporated by reference.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "apoptotic neurodegeneration" as used herein refers to degeneration of neuronal cells (e.g., CNS neurons, primary neuron cultures, neuronal cell lines) which is causally linked to an apoptotic stimulus such as accumulation of a neurotoxic substance (e.g., an amyloidogenic polypeptide other than Aβ) or a reduction of a necessary growth factor (e.g., NGF, BDNF, CTNF, etc.) which effects neuronal apoptosis. Such apoptosis may be manifested in the neuronal cells by direct interaction with an amyloidogenic polypeptide other than Aβ peptide or via indirect effects resulting from interaction of an amyloidogenic polypeptide other than Aβ on neuronal-associated cells (e.g., astrocytes, astrocytoma cells, microglial cells, monocytes, etc.). Such indirect effects may involve nitric oxide formation, excitatory amino acid mimetics, and/or cytokine production by the non-neuronal calls, whereby such compounds produce neuronal cell damage. Some neuropathologies may be causally associated with aberrant forms or amounts of extracellular proteins other than Aβ; these neuropathologies are also defined herein as amyloidogenic polypeptide-mediated neurodegenerative diseases for purposes of this specification; for illustration, an example of such a type of neuropathology is Creutzfeldt-Jakob disease.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "active agent" is used herein to refer to an agent which is identified by one or more screening method(s) of the invention as an agent which inhibits PLA$_2$ activity and retards or reduces apoptotic neurodegeneration. Active agents can be sold as commercial reagents for standardizing toxicological or pharmaceutical evaluations which employ neuron cultures or transgenic animals which exhibit neurodegenerative pathology. Some active agents will have therapeutic potential as drugs for human use, such as being administered to patients or individuals ascertained to be predisposed to developing degenerative neuropathology (e.g., Creutzfeldt-Jakob disease, Huntington's disease, stroke patients). Active agents are often small (<3,000 Daltons) organic molecules, but may be macromolecules (e.g., polypeptides, polynucleotides, etc.), inorganic compounds, including metal salts. A selective inhibitor of PLA$_2$ produces a preferential inhibition of PLA$_2$ as compared to inhibition of other mammalian phospholipases; such that the concentration required to produce inhibition of 50% of PLA$_2$ catalytic activity is at least one order of magnitude lower than the concentration required to produce inhibition of 50% of the catalytic activity of phospholipases other than PLA$_2$. A selective inhibitor of cPLA$_2$ produces a preferential inhibition of cPLA$_2$ as compared to inhibition of other mammalian PLA$_2$ enzymes.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as active agents by inclusion in screening assays described hereinbelow. Agents may be selected from a combinatorial compound library for the capacity to interact with and/or inhibit PLA$_2$. The agent library may be naive or may be composed of structural analogs of known PLA$_2$ inhibitors, or a combination of both. Example agents of a type known to inhibit PLA$_2$ would include arachidonic acid derivatives and analogs (e.g., arachidonyl trifluoromethyl ketone), benzenesulfonamides, aminosteroids, bromoenol lactone, manoalide, p-bromophenacyl bromide, minocycline, doxycycline, 7,7,-dimethyl-5,8-eicosadienoic acid, quinacrine, and the like, among others known in the art. Examples are: N-cycloheptyl-4-[N-methyl-N-[(E)-3-(4-methylsulfonylphenyl)-2-propenoyl]amino]benzenesulfonamide (AN20606) and N-cyclohepyl4-[N-methyl-N[(E)-3-(4-cyanophenyl0-2-propenoyl]amino]benzenesulfonamide (AN20628).

The term "PLA$_2$" as used herein refers to a naturally-occurring mammalian PLA$_2$ polypeptide having enzymatic activity. A paradigmatic PLA$_2$ can be considered to be human cPLA$_2$ substantially equivalent to that such as that described in U.S. Pat. 5,354,677; 5,328,842; Clark et al. (1991) Cell 65: 1043, and Sharp et al. (1991) J. Biol. Chem. 266: 14850, or the cognate cPLA$_2$ enzyme in a non-human mammalian species. PLA$_2$ activity is present in a variety of cytosolic and extracellular PLA$_2$ polypeptide species. A preferred PLA$_2$ polypeptide of the invention is a cytosolic PLA$_2$, such as cPLA$_2$, and typically a calcium-activable cPLA$_2$ which is activated (exhibits enhanced catalytic activity) by the presence of calcium ions (Ca$^{+2}$)

The term "amyloidogenic polypeptidell refers to polypeptides which form extracellular deposits and/or intracellular inclusions, and/or which have the property of producing neurotoxicity on neuronal cell cultures and/or primary neurons, typically in the presence of microglial cells and/or astrocytic cells and/or monocytes, or directly; as used in this disclosure, amyloidogenic polypeptides are not products of the APP gene or fragments thereof (e.g., Aβ peptide). Sipe, JD (1992) Ann. Rev. Biochem. 61: 947 provides a review of several known amyloidogenic polypeptides. For illustration, mellitin is an amyloidogenic polypeptide for purposes of the invention as its contact with neuronal cell cultures induces apoptotic neurodegeneration of the neuronal cells, even if detectable amyloid deposits are not formed.

Neurotoxicity of any amyloidogenic polypeptide can be determined by assay for neuronal cell viability according to the methods of the invention and according to methods known in the art. Typically, neurotoxicity of an amyloidogenic polypeptide will be dose-dependent.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are the most highly homologous match between the two species and both genes encode a protein which functions similarly (e.g., in signaling T cell activation through MHC class II-restricted antigen recognition).

As used herein, the term "xenogenic" is defined in relation to a recipient mammalian host cell or nonhuman animal and means that an amino acid sequence or polynucleotide sequence is not encoded by or present in, respectively, the naturally-occuring genome of the recipient mammalian host cell or nonhuman animal. Xenogenic DNA sequences are foreign DNA sequences; for example, a human cPLA$_2$ gene is xenogenic with respect to murine ES cells; also, for illustration, a human cystic fibrosis-associated CFTR allele is xenogenic with respect to a human cell line that is homozygous for wild-type (normal) CFTR alleles. Thus, a cloned murine nucleic acid sequence that has been mutated (e.g., by site directed mutagenesis) is xenogenic with respect to the murine genome from which the sequence was originally derived, if the mutated sequence does not naturally occur in the murine genome.

As used herein, a "heterologous gene" or "heterologous polynucleotide sequence" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate gene found in an organism not consisting of the transgenic nonhuman animal. Thus, a transgenic mouse harboring a human cPLA$_2$ gene can be described as harboring a heterologous cPLA$_2$ gene. A transgene containing various gene segments encoding a heterologous protein sequence may be readily identified, e.g. by hybridization or DNA sequencing, as being from a species of organism other than the transgenic animal. For example, expression of human cPLA$_2$ amino acid sequences may be detected in the transgenic nonhuman animals of the invention with antibodies specific for human cPLA$_2$ epitopes encoded by human cPLA$_2$ gene segments. A cognate heterologous gene refers to a corresponding gene from another species; thus, if murine cPLA$_2$ is the reference, human cPLA$_2$ is a cognate heterologous gene (as is porcine, ovine, or rat cPLA$_2$, along with cPLA$_2$ genes from other species). A mutated endogenous gene sequence can be referred to as a heterologous gene; for example, a transgene encoding a murine cPLA$_2$ comprising a mutation (which is not known in naturally-occurring murine genomes) is a heterologous transgene with respect to murine and non-murine species.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of a mammalian PLA$_2$ gene, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into an host cell endogenous gene locus by homologous recombination between a targeting construct homology region and said endogenous gene locus sequence. If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J. NIH Res.* 3: 59; Hasty et al. (1991) *Nature* 350; 243, which are incorporated herein by reference), the targeting region is only transiently incorporated into the endogenous gene locus and is eliminated from the host genome by selection. A targeting region may comprise a sequence that is substantially homologous to an endogenous gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous gene sequence, which can include sequences flanking said gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence.

The terms "functional disruption" or "functionally disrupted" as used herein means that a gene locus comprises at least one mutation or structural alteration such that the functionally disrupted gene is incapable of directing the efficient expression of functional gene product. The invention encompasses knockout animals, such as mice, which are homozygous for a functionally disrupted $PLA_2$ gene, typically a $cPLA_2$ gene. For example but not limitation, an endogenous $cPLA_2$ gene that has a neo gene cassette integrated into an exon (e.g., the second exon) of a $cPLA_2$ gene, is not capable of encoding a functional protein (isoform) that comprises the inactivated exon, and is therefore a functionally disrupted cPLA$_2$ gene locus. Also for example, a targeted mutation in the exons of an endogenous cPLA$_2$ gene may result in a mutated endogenous gene that can express a truncated PLA$_2$ protein. Functional disruption can include the complete substitution of a heterologous cPLA$_2$ gene locus in place of an endogenous cPLA$_2$ locus, so that, for example, a targeting transgene that replaces the entire mouse cPLA$_2$ locus with a human cPLA$_2$ allele, which may be functional in the mouse, is said to have functionally disrupted the endogenous murine cPLA$_2$ locus by displacing it. Preferably, at least one exon which is incorporated into the mRNAs encoding most or all of the cPLA$_2$ isoforms are functionally disrupted. Deletion or interruption of essential transcriptional regulatory elements, polyadenylation signal (s), splicing site sequences will also yield a functionally disrupted gene. Functional disruption of an endogenous cPLA$_2$ gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, cPLA$_2$ alleles that are structurally disrupted are consequently functionally disrupted, however cPLA$_2$ alleles may also be functionally disrupted without concomitantly being structurally disrupted, i.e., by targeted alteration of a nonexon sequence such as ablation of a promoter. An allele comprising a targeted alteration that interferes with the efficient expression of a functional gene product from the allele is referred to in the art as a "null allele" or "knockout allele".

DETAILED DESCRIPTION

Overview

A basis of the present invention is the unexpected finding that apoptotic neuronal cell degeneration is mediated by a biochemical cascade which requires PLA$_2$ activity, an enzyme which catalyzes the hydrolysis of the fatty acid ester bond at the sn-2 position of membrane phospholipids to produce arachidonic acid and its metabolites, and in the case of the cytosolic form, cPLA$_2$, also produces lysophospholipids. Agents which selectively block PLA$_2$ activity in neurons (such as neuronal cell lines and cultured neurons) and/or glial cells (including glial cell lines) can be used to inhibit apoptotic neuronal degeneration, such as that which results from exposure of such cells to amyloidogenic polypeptides or other apoptotic stimulus (e.g., growth factor withdrawal), such as Creutzfeldt-Jakob Disease and related neurodegenerative conditions discussed herein and the like. These selective PLA$_2$-blocking agents can be used to inhibit and/or retard neuronal degeneration.

Cellular models of apoptotic neuropathology are based on the ability of an amyloidogenic polypeptide and/or growth factor withdrawal to induce neuronal degeneration in cultured human and rodent cell populations (neurons, neuronal cell lines, microglia, microglial cell lines, astrocytes, astrocytoma cells and cell lines, monocytes and monocytic cell lines) and neuronal and glial cell lines, wherein the biological changes mimic the neuropathological changes associated with a human neurodegenerative disease.

A basis of the invention is the unexpected observation that several structurally dissimilar inhibitors of PLA$_2$ were capable of inhibiting apoptotic neuronal degeneration in such cellular models of AD. Based on this observation and others made by Applicants, it is believed that PLA$_2$ activity is an essential component of neuropathological changes, such as those which occur in human neurodegenerative diseases. Active agents which inhibit PLA$_2$ activity are expected to inhibit such neuropathological changes.

Phospholipase A$_2$

Phospholipases A$_2$ (PLA$_2$s; EC 3.1.1.4) are enzymes that hydrolyze the 2-acyl ester bond of phosphoglycerides generating free fatty acids and lysophospholipids (for review, see, Kramer, R. M. (1993) *Advances in Second Messenger and Phosphoprotein Research* 28: 81; Glaser et al. (1993) *TiPS* 14: 92; Dennis EA (1994) *J. Biol. Chem.* 269: 13057). PLA$_2$s are a diverse class of enzymes with regard to function, localization, regulation, mechanism, sequence, structure, and role of divalent metal ions.

In general, PLA$_2$ enzymes catalyze the hydrolysis of the fatty acid ester bond at the sn-2 position of membrane phospholipids to produce arachidonic acid and its metabolites. A variety of polypeptide species can exhibit PLA$_2$ activity; for purposes of this specification, these polypeptides are considered PLA$_2$ isozymes.

Group I, II, and III PLA$_2$s are extracellular enzymes of approximately 14–18 kD in humans, and are designated sPLA$_2$s, in recognition of their secretion. sPLA$_2$s are found in many extracellular fluids and have a broad substrate specificity for many types of phospholipids.

Group IV PLA$_2$ is a cytosolic enzyme of approximately 85 kD (based on deduced cDNA coding sequence) to 110 kD (based on SDS-PAGE of purified protein), and is designated cPLA$_2$ to indicate its cytosolic location. Unlike sPLA$_2$s, the cPLA$_2$ enzyme exhibits preferential catalysis of phospholipids which contain arachidonic acid, and is most likely the enzyme responsible for arachidonic acid release which is the rate-limiting step for subsequent eicosanoid biosynthesis of proinflammatory lipid mediators (prostaglandins, leukotrienes, lipoxins, and platelet-activating factor: "PAF").

Other PLA$_2$ activities, both cytosolic and extracellular, are less well-characterized with regard to macromolecular identification and polypeptide sequences.

cPLA$_2$ is present in the cytosol of a variety of species and cell types, including human U937 cells (monocytes), platelets, kidney, and macrophages, among others, and is implicated in controlling arachidonic acid metabolism and eicosanoid production.

Human cPLA$_2$ has been cloned as a cDNA isolated from mRNA of a human monocytic cell line (U.S. Pat. Nos. 5,354,677 and 5,328,842; Sharp et al. (1991) op.cit; Clark et al. (1991) op.cit) and the mPNA encodes a protein of 749 amino acids which has little detectable homology with the secreted sPLA$_2$S or any other protein in known sequence databases. The cPLA$_2$ CDNA identifies a single copy gene in the human genome, with no detectable closely related genes based on Southern blotting experiments.

cPLA$_2$ contains an amino-terminal domain which binds calcium and similar divalent cations, and cPLA$_2$ binds to membrane vesicles at submicromolar concentrations of Ca$^{+2}$ in a calcium-dependent fashion. cPLA$_2$ can translocate to membranes when activated in the presence of calcium. Presumably, cPLA$_2$ associates with membrane components in vivo under suitable calcium concentrations. Agents that stimulate the release of arachidonic acid (ATP, thrombin, phorbol ester, calcium ionophore) can cause increased serine phosphorylation of cPLA$_2$ which increases the enzymatic activity of cPLA$_2$ (Lin et al. (1993) *Cell* 72: 269). Phosphorylation is believed to contribute to the control of cPLA$_2$ activity in vivo (Lin et al. (1992) *Proc. Natl. Acad. Sci.*

*(USA)* 89: 6147; Lin et al. (1993) *Cell* 72: 269; Qiu et al. (1993) *J. Biol. Chem.* 268: 24506; Kramer et al. (1993) *J. Biol. Chem.* 268: 26796).

Antibodies have been raised against human $cPLA_2$ and crossreact with $cPLA_2$ from a variety of animals, indicating conservation of structure between species. Anti-$cPLA_2$ antibodies identify the presence of $cPLA_2$ in lung, brain, testis, kidney, spleen, liver, and heart, although the precise role of $cPLA_2$ in the metabolism of each of these tissues is not known (see, EP 0501779).

The art generally recognizes the physiologic role of $cPLA_2$ to be in the mediation of inflammation via its role in arachidonic acid metabolism and lipid/lipoprotein metabolism, such as cell membrane homeostasis. Roshak et al. (1994) *J. Biol. Chem.* 269: 25999 used antisense oligonucleotides complementary to the $cPLA_2$ mRNA to inhibit prostaglandin production in LPS-induced monocytes, indicating a potential role for $cPLA_2$ in generating inflammatory regulators in monocytes. Verity MA (1993) *Ann. N.Y. Acad. Sci.* 679: 110 speculates that "abusive activation" of $PLA_2$ via uncontrolled $Ca^{+2}$ influx might produce irreversible cell injury of neurons via extensive localized lipid peroxidation and subsequent membrane disintegration. U.S. Pat. Nos. 5,354,677 and 5,328,842 indicate that $cPLA_2$ inhibitors are expected to be used to treat inflammatory conditions, such as psoriasis, asthma, and arthritis (see, col. 15), and prophesizes that such anti-inflammatory compounds can be identified as $cPLA_2$ inhibitors.

A number of inhibitors of $PLA_2$ activity have been reported. Bromoenol lactone and trifluoromethyl ketones (e.g., palmitoyl trifluoromethyl ketone, arachidonyl trifluoromethyl ketone) have been reported to be capable of inhibiting a $Ca^{+2}$-independent $PLA_2$ activity (Ackermann et al. (1995) *J. Biol. Chem.* 270: 445) as well as $cPLA_2$ (Street et al. (1993) *Biochemistry* 32: 5935). Several benzenesulfonamide derivatives have also been reported to be capable of inhibiting $PLA_2$ activity (European Patent Application 468 054; Oinuma et al. (1991) *J. Med. Chem.* 34: 2260). Hazen et al. (1991) *J. Biol. Chem.* 266: 7227 report a compound that is an irreversible inhibitor of myocardial calcium-indenpendent $PLA_2$ activity. Pruzanski et al. report minocycline and doxycycline are inhibitors of $PLA_2$ activity.

Reynolds et al. (1994) *Anal. Biochem.* 217: 25 describe a convenient microtiter plate assay for $cPLA_2$. Currie et al. (1994) *Biochem. J.* 304: 923, describe a $cPLA_2$ assay for assaying $cPLA_2$ activity from activated whole cells. This assay can be adapted for assay of related $PLA_2$ activity, whether from $cPLA_2$ or other $PLA_2$ enzymes having similar catalytic activities.

A suitable source of $cPLA_2$ can be obtained, if desired, by expression of a recombinant expression vector in a suitable host cell, as described in U.S. Pat. No. 5,354,677, or by conventional biochemical purification from mammalian cells, as is known in the art.

Methods for Identifying Neurodegeneration Inhibitors

One method to identify active agents which inhibit the development of neuropathology is simply brute force screening of all possible chemical structures in a suitable cellular and/or animal model of apoptotic neurotoxicity. Unfortunately, the complexity and structural potential of chemistry makes a thorough search of all of the chemical structural space impossible, even if facile synthetic methods were available for all potential compounds. Because an exhaustive search of chemical space is not possible, it is exceedingly important to identify properties of likely inhibitors of neurodegenerative processes involved in amyloidogenic polypeptide neurotoxicity and related diseases.

In order to expedite the screening of compound libraries and to increase the probability of obtaining active agents which inhibit neurodegeneration, it is desirable to preselect compounds which are known or suspected inhibitors of $PLA_2$ (based on structural homology to substrates or inhibitors), and preferably are selective inhibitors of cytosolic $PLA_2$. The $PLA_2$ inhibitors are typically identified by initially employing a $PLA_2$ assay, which may comprise an in vitro $PLA_2$ enzyme assay using a standardized amount of a purified or recombinantly produced mammalian $PLA_2$, such as human $cPLA_2$, and/or may comprise a whole cell assay, or a combination thereof. For example and not limitation, a primary $PLA_2$ assay can be performed essentially according to Reynolds et al. (1994) *Anal. Biochem.* 217: 25, with an agent added to test assay reactions and compared to a control reaction lacking an added agent. Agents which are found to inhibit $PLA_2$ activity in the assay are then selected for subsequent testing in a secondary assay. An alternative primary assay can optionally comprise a whole cell $PLA_2$ assay, such as that disclosed in Currie et al. (1994) *Biochem. J.* 304: 923. Other suitable assays for measuring the capacity of an agent to inhibit $PLA_2$ will be apparent to those in the art in view of Applicants' specification, and also with reference to U.S. Pat. Nos. 5,354,677 and 5,328,842, incorporated herein by reference. The primary $PLA_2$ assays can also be multiplexed, so that agents which are positively identified in one primary assay are verified as bona fide $PLA_2$ inhibitors in another type of primary assay. Preferably, the $PLA_2$ activity is a cytosolic $PLA_2$ enzyme, most typically a calcium-dependent $cPLA_2$.

Agents selected in the primary assay(s) as $PLA_2$ inhibitors are evaluated for their capacity to inhibit neuronal degeneration and/or microglial and/or astrocyte (astrocytoma cells) and/or monocyte activation in mammalian cortical or hippocampal cell cultures or neuronal cell line cultures, mixed neuronal/glial cultures, or the like, treated with an amyloidogenic polypeptide or growth factor withdrawal as described in the Examples, or by other suitable neurotoxicity assays for measuring apoptotic neurodegeneration. These secondary assays measure the ability of a selected agent to inhibit neurodegeneration in neurodegenerative disease models. Typically, a secondary assay is performed using a primary rat or human cortical or hippocampal neuron culture and/or a rat or human cortical or hippocampal astrocyte/microglia culture, as described herein; alternatively, a neuronal cell line can be employed, typically with (1) primary glial cells and/or a glial cell line, and/or (2) primary astrocytes and/or an astrocytic cell line (astrocytoma cells). However, other suitable neurodegeneration models can be employed, such as transgenic mice expressing an amyloidogenic polypeptide and exhibiting neuropathology (e.g., a PrP transgenic mouse). A plurality of secondary assays may also be multiplexed, so that for example agents which score positive as in a neuronal cell culture neurodegeneration inhibition assay can be tested in a mammalian model of neurodegenerative disease (e.g., a transgenic mouse PrP model), and vice versa.

Thus, a primary screening assay to identify $PLA_2$ inhibitors is performed prior to a secondary screening assay to identify neurodegeneration inhibitors. An advantage of this approach is that is substantially reduces the chemical structure space which needs to be searched to identify neurodegeneration inhibitors. Furthermore, several structural families of $PLA_2$ inhibitors are known, whereas there is no known inhibitor of neurodegeneration which is substantially effective as a human therapeutic; thus the agent search can be focused to compounds likely to be $PLA_2$ inhibitors based on their structural homology to identified $PLA_2$ inhibitors or to $PLA_2$ inhibitors prophesized by rational design based on the known $PLA_2$ protein structures, such as human $cPLA_2$.

Agents

A bank or library of agents is selected at the discretion of the practitioner. Typical agents will be structural congeners of known $PLA_2$ inhibitors, or compounds rationally predicted to have $PLA_2$ inhibition activity. In some, embodiments random or pseudorandom agent libraries can be employed, as can combinatorial chemistry libraries, peptide/peptoid libraries, and the like.

In general, agents such as: aminosteroids (e.g., 21-aminosteroids), (e)-6-(bromomethylene)tetrahydro-3-(1naphthalenyl)-2H-pyran-2-one, or the like, and halogenated methylketones of arachidonic acid or palmitic acid, or the like, can be suitable $PLA_2$ inhibitors. These compounds are are suitable for use as agents, especially to obtain irreversible $PLA_2$ inhibitors which may have an advantageous duration of action. Benzenesulfonamides and various arylsulfonamides are also suitable agents to include in a compound library of the invention. Typically, such compounds are selected from the group of known chemical compounds known in the chemical and pharmaceutical literature; from described compound libraries; from natural compounds which may comprise undetermined structures; and from other suitable sources of chemical diversity.

Essentially any type of agent desired by the practitioner may be evaluated using the method, although agents believed likely to have $PLA_2$ inhibition activity are typically preferred.

Examples of the types of compounds believed to be preferable for inclusion in agent libraries include: BIRM 270 (Farina et al. (1994) *J. Pharmacol Exp. Therap.* 271: 1418; Ro23-9358 (LeMahieu et al. (1993) *J. Med. Chem.* 36: 3029; U73122 (Chen et al. (1995) *Life Sciences* 56: 103); BMS-181162 (Tramposch et al. (1994) *J. Pharmacol. Exp. Therap.* 271: 852; Burke et al. (1995) *J. Biol. Chem.* 270: 274); and "Compound 1" (Abdullah et al. (1995) *Bioorganic and Medicinal Chem. Let.* 5: 519); Hazen et al. (1991) *J. Biol. Chem.* 266: 7227, among others.

Agents which are identified as active agents for $PLA_2$ inhibition and inhibition of neurodegeneration are administered to cell populations comprising neuronal cells to reduce or arrest neuronal cell death via $PLA_2$-dependent pathways.

The agents can be any molecule, compound, or other substance which can be added to the cell culture or administered to a test animal without substantially interfering with cell or animal viability. Suitable test agents may be small molecules, biological polymers, such as polypeptides, polysaccharides, polynucleotides, and the like. The test compounds will typically be administered to transgenic animals at a dosage of from 1 ng/kg to 10 mg/kg, usually from 1 µg/kg to 1 mg/kg.

In one aspect, active agents are able to cross the blood-brain barrier of a human to produce a therapeutically efficacious concentration in cerebrospinal fluid and CNS tissues (e.g., cortical neurons). Other approaches to enhancing delivery of drugs, particularly across the blood-brain barrier, utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily transported across the blood-brain barrier. Pardridge and Schimmel, U.S. Pat. No. 4,902,505, disclose chimeric peptides for enhancing transport by receptor-mediated transcytosis.

Disease Model Systems

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

In one aspect of the invention are provided nonhuman animals harboring at least one copy of a transgene comprising a polynucleotide sequence which encodes a heterologous $PLA_2$ polypeptide operably linked to a transcription regulatory sequence capable of producing expression of the heterologous $PLA_2$ polypeptide in the transgenic nonhuman animal. Said heterologous $PLA_2$ polypeptide is expressed in cells which normally express the naturally-occurring endogenous $PLA_2$ gene (if present). Typically, the nonhuman animal is a mouse and the heterologous $PLA_2$ gene is a human $PLA_2$ gene, such as the human $cPLA_2$ gene. Such transgenes typically comprise a $PLA_2$ expression cassette, wherein a linked promoter and, preferably, an enhancer drive expression of structural sequences encoding a heterologous $PLA_2$ polypeptide in neuronal cell types. Often, the mouse $cPLA_2$ gene is the inactivated target gene and optionally includes a transgene encoding a human $cPLA_2$ polypeptide having $PLA_2$ activity.

The invention also provides transgenes comprising a gene encoding a human $PLA_2$, said gene operably linked to a transcription regulatory sequence functional in the host transgenic animal (e.g., a neural-specific promoter). Such transgenes are typically integrated into a host chromosomal location by nonhomologous integration. The transgenes may further comprise a selectable marker, such as a neo or gpt gene operably linked to a constitutive promoter, such as a phosphoglycerate kinase (pgk) promoter or HSV tk gene promoter linked to an enhancer (e.g., SV40 enhancer).

The invention further provides nonhuman transgenic animals, typically nonhuman mammals such as mice, which harbor at least one copy of a transgene or targeting construct of the invention, either homologously or nonhomologously integrated into an endogenous chromosomal location so as to encode a human $PLA_2$ polypeptide. Such transgenic animals are usually produced by introducing the transgene or targeting construct into a fertilized egg or embryonic stem (ES) cell, typically by microinjection, electroporation, lipofection, or biolistics. The transgenic animals express the human $PLA_2$ gene of the transgene (or homologously recombined targeting construct), typically in brain tissue. Such animals are suitable for use in a variety of disease model and drug screening uses, for sales to commercial laboratories conducting toxicological evaluation of compounds believed likely of producing chronic neuronal toxicity, as well as other applications.

The invention also provides nonhuman animals and cells which harbor at least one integrated targeting construct that functionally disrupts an endogenous $PLA_2$ gene locus, typically by deleting or mutating a genetic element (e.g., exon sequence, splicing signal, promoter, enhancer) that is required for efficient functional expression of a complete gene product.

The invention also provides transgenic nonhuman animals, such as a non-primate mammal, that have at least one inactivated endogenous $PLA_2$ allele, and preferably are homozygous for inactivated $PLA_2$ alleles, and which are substantially incapable of directing the efficient expression of endogenous (i.e., wildtype) $PLA_2$. For example, in a preferred embodiment, a transgenic mouse is homozygous for inactivated endogenous $PLA_2$ alleles and is substantially incapable of producing murine $PLA_2$ encoded by a endogenous (i.e., naturally-occurring) $PLA_2$ gene. Such a transgenic mouse, having inactivated endogenous $PLA_2$ genes, is a preferred host recipient for a transgene encoding a heterologous $PLA_2$ polypeptide, preferably a human $PLA_2$ polypeptide. For example, human $PLA_2$ may be encoded and expressed from a heterologous transgene(s) in such transgenic mice. Such heterologous transgenes may be integrated in a nonhomologous location in a chromosome of the nonhuman animal, or may be integrated by homologous recombination or gene conversion into a nonhuman $PLA_2$ gene locus, thereby effecting simultaneous knockout of the endogenous $PLA_2$ gene (or segment thereof) and replacement with the human $PLA_2$ gene (or segment thereof). A preferred $PLA_2$ gene is the $cPLA_2$ gene.

Such animals are suitable for use in a variety of disease model and drug screening uses, for sales to commercial laboratories conducting toxicological evaluation of compounds believed likely of producing chronic neuronal toxicity, as well as other applications.

An animal model of Parkinson's disease involving iatrogenic hydroxyl radical generation by MPTP (Chiueh et al. (1992) Synapse 11: 346, incorporated herein by reference) was used to evaluate the protective effect of C7 on free radical-induced damage. The neurotoxin, MPTP, has been shown to lead to the degeneration of dopaminergic neurons in the brain, thus providing a model of experimentally induced Parkinson's disease (e.g., iatrogenic toxicity). This model is now widely accepted in the art and is used for evaluating potential therapeutic agents for this disease.

Particular techniques for producing transgenic mice which express an amyloidogenic polypeptide, and other neurodegenerative disease animal models are described elsewhere in the art. It will be appreciated that the preparation of other transgenic animals expressing an amyloidogenic polypeptide may be accomplished, including rats, hamsters, guinea pigs, rabbits, and the like. The effect of test compounds on $PLA_2$ activity in test animals may be measured in various specimens from the test animals.

Antisense Polynucleotides

Additional embodiments directed to modulation of $PLA_2$ activity include methods that employ specific antisense polynucleotides complementary to all or part of the human or mouse $PLA_2$ sequences, such as antisense polynucleotides to the human $cPLA_2$ gene or mRNA. Such complementary antisense polynucleotides may include nucleotide substitutions, additions, deletions, or transpositions, so long as specific hybridization to the relevant target sequence corresponding to human or mouse $PLA_2$ cDNA is retained as a functional property of the polynucleotide. Complementary antisense polynucleotides include soluble antisense RNA or DNA oligonucleotides which can hybridize specifically to $PLA_2$ mRNA species and prevent transcription of the mRNA species and/or translation of the encoded polypeptide (Ching et al. (1989) Proc. Natl. Acad. Sci. U.S.A. 86: 10006; Broder et al. (1990) Ann. Int. Med. 113: 604; Loreau et al. (1990) FEBS Letters 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of $PLA_2$ polypeptides. Since $PLA_2$ protein expression is associated with activation and enzymatic activity, antisense polynucleotides that prevent transcription and/or translation of mRNA corresponding to $PLA_2$ polypeptides may inhibit $PLA_2$ activity and/or reverse the degeneration of neuronal and/or microglial cells and/or astrocytic cells and/or monocytic cells. Compositions containing a therapeutically effective dosage of $PLA_2$ antisense polynucleotides may be administered for treatment of neurodegenerative diseases, if desired. Antisense polynucleotides of various lengths may be produced, although such antisense polynucleotides typically comprise a sequence of about at least 25 consecutive nucleotides which are substantially identical to a naturally-occurring $PLA_2$ polynucleotide sequence, and typically which are identical to a human $PLA_2$ sequence, such as human $cPLA_2$.

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the cerebrospinal fluid or direct brain application in vivo. Soluble antisense polynucleotides present in the external milieu have been shown to gain access to the cytoplasm and inhibit translation of specific mRNA species and/or transcription of specific genes. In some embodiments the antisense polynucleotides comprise methylphosphonate moieties or are polyamide nucleic acids (PNAs). For general methods relating to antisense polynucleotides, see Antisense RNA and DNA, (1988), D. A. Melton, Ed., Cold Spring Harbor Laboratory, Cold Spring Harbor, N.Y.).

Neurodegenerative Disease

Neurodegenerative diseases are exemplified, but not limited to: Lewy Body disease, degeneration resulatant from cerebral ischemia, ALS, prion-related disease (Creutzfedlt-Jakob, kuru, etc.), Parkinson's disease, multiple sclerosis, hereditary ataxia, Shy Drager Syndrome, Progressive Supranuclear Palsy, Huntington's disease, spinal muscular atrophy (Types I, II, and III), Reye's Syndrome, status epilepticus, progressive multifocal leukoencephalopathy, viral encephalitis, normal pressure hydrocephalus, subacute sclerosing panencephalitis, head and spinal cord trauma post-injury degeneration, frontal lobe dementia, poliomyelitis and postpolio neuropathy, glaucoma, and various neuropathies (autonomic, Guillan-Barre, diabetic, porphyria, autoimmune, vasculitis, among others.

Neurodegenerative diseases associated with amyloidogenic polypeptides include but are not limited to:

Prion-related diseases (e.g., Creutzfeldt-Jakob disease, scrapie, Kuru);

Transthyretin (TTR)-induced polyneuropathies (including, but not limited to: Portuguese, Japanese, Swedish, Illinois-German, Swiss-Indiana, Maryland-German, Appalachian-Israel);

ApoA1-induced polyneuropathy (e.g., Iowa variant);

Gelsolin-inauced polyneuropathy (e.g., Finnish variant); Icelandic Hemorrhage angiopathy due to cystatin C disease;

Serum AA amyloid polyneuropathy as seen in familial Mediterranean fever, and other conditions that cause AA amyloidosis, such as leprosy, tuberculosis, rheumatoid arthritis; and Immunoglobulin/light chain amyloid polyneuropathy as seen in multiple myeloma and primary amyloidosis; among others.

It is believed that these diseases and other neurodegenerative diseases can be treated by administration of a therapeutically efficacious dose of a suitalble $PLA_2$ inhibitor. Such administration will often require chronic dosing. Other neurodegenerative diseases are described in: 19th Edition: *Cecil Textbook of Medicine*, Wyngaarden, Smith and Bennett, eds. 1992, W.B. Saunders, Philadelphia, Pa.

Compositions of Neurodegeneration Inhibitors

Active, agents which are $PLA_2$ inhibitors and also inhibit neuronal degeneration in neurodegenerative disease models can be used to retard or reduced neuropathology in vivo. Thus, the present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pennsylvania, 16th Ed., 1982, the disclosure of which is incorporated herein by reference.

The pharmaceutical compositions just described are suitable for systemic administration to the host, including both parenteral, topical, and oral administration, including intracranial administration. Thus, the present invention provides compositions for administration to a host, where the compositions comprise a pharmaceutically acceptable solution of the identified $PLA_2$-inhibitory compound in an acceptable carrier, as described above. Such formulations can be used therapeutically on mammals having AD-type neuropathology or disease progression of a related neurodegenerative disease.

Compositions containing the present $PLA_2$ inhibitors can be administered for prophylactic and/or therapeutic treatments of neurodegenerative disease. In therapeutic application, compositions are administered to a patient already affected by the particular neurodegenerative disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 10 g of $PLA_2$ inhibitor per dose, with dosages of from 10 mg to 2000 mg per patient being more commonly used. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences.

The invention also provides the use of a $PLA_2$ inhibitor to slow, arrest, or reverse the development of a neurodegenerative disease in a human patient; an efficacious amount of the $PLA_2$ inhibitor is administered to the patient to inhibit progression of the disease.

The following examples are provided for illustration and are not intended to limit the invention to the specific example provided.

EXPERIMENTAL EXAMPLES

General Methods

Tissue Culture Methods

PC12 cell cultures

Stock cell cultures were maintained in RPMI 1640 medium supplemented with 10% heat-inactivated horse serum and 5% fetal bovine serum. Experiments in serum-free medium were performed as previously described (Rukenstein et al. (1991), J. Neurosci. 11:2552–2563) except the cells were plated at a density of $25-100 \times 10^3$ cells per well in 96-well plastic culture dishes (surface area 0.4 $cm^2$). The bottom surfaces of the wells were precoated with rat-tail collagen as described elsewhere (Green and Tischler (1982), Adv. Cell Neurobiol. 3:373–414), and the volume of the medium per well was 100 µl.

Rat superior cervical ganglion neurons

Postnatal day 1–3 rat superior cervical ganglion (SGC) cell were dissociated and plated as previously described (Lee et al. (1980), Neuroscience 5:2239–2245) at a density of 0.5 ganglion per well in 96-well plastic culture plates (surface area 0.4 $cm^2$). Neurons were maintained in 200 pl of culture medium (Eagles' MEM with Earle's salts, 10% fetal bovine serum, 2 mM L-glutamine, 100 µg/ml streptomycin, and 100 U/ml penicillin, and 100 ng/ml nerve growth factor (NGF). The growth of nonneuronal cells (i.e., fibroblasts and Schwann cells) was inhibited by the addition of 20 µM uridine and 20 µM fluorodeoxyuridine). Neurons were deprived of NGF by replacing the NGF-containing medium with the same medium, except that a polyclonal goat anti-NGF antiserum was substituted for NGF. Neuronal survival was determined 24–30 hours after NGF deprivation by visual inspection using phase-contrast light microscopy.

Cell Survival Assays

AlamarBlue™ assay

The alamarBlue™ assay incorporates a proprietary fluorometric/colorimetric metabolic indicator (Alamar Biosciences, Inc.). Viable cells convert alamarBlue™ from an oxidized (non-fluorescent, blue) form to a reduced (fluorescent, red) form. Assays were performed by replacing the culture media with a 10% alamarBlue™ solution in RPMI (PC12 cells) or DMEM (rat cortical neurons). Reduction of alamarBlue™ was determined spectrofluorometrically using a Millipore Cytofluro 2350 Scanner (excitation, 560 nm, emission, 590 nm) and CytoCalc™ software (Millipore Corporation). Neuronal viability as assessed by alamarBlue™ was comparable to that obtained by measuring the fluorogenic probe Calcein AM, the release of the cytoplasmic enzyme lactate dehydrogenase (LDH), or the reduction of the tetrazolium salt, 2,3-bis(2-methoxy-4-nitro-5-sulfophenyl)-2H-tetrazolium-5-carboxanilde (XTT).

Lactate dehydrogenase (LDH) kinetic assay

The LDH kinetic assay utilized LD-L 10 reagent (Sigma #228-10). 20 µl of culture supernatant was assayed using 200 µl of reconstituted LD-L 10 reagent. Samples were read every 30 seconds over a 5 minute time period using a kinetic microplate reader ($UV_{max}$, Molecular Devices) and SOFTmax® version 2.32 FPU software. Absorbance at 340 nm minus 650 nm was used to determine the rate of formation of reduced nicotinamide adenine dinucleotide (NADH). The reaction rate was linear over this time period. The rate of reduced NADH formation is directly proportional to LDH activity in the sample. Fluorescent values were converted to U/ml by the inclusion of a LDH standard curve on each assay plate using LDH controls (Sigma # S2005 and S1005).

Example 1: Mellitin-Induced Neurodegeneration

Figure 1A:
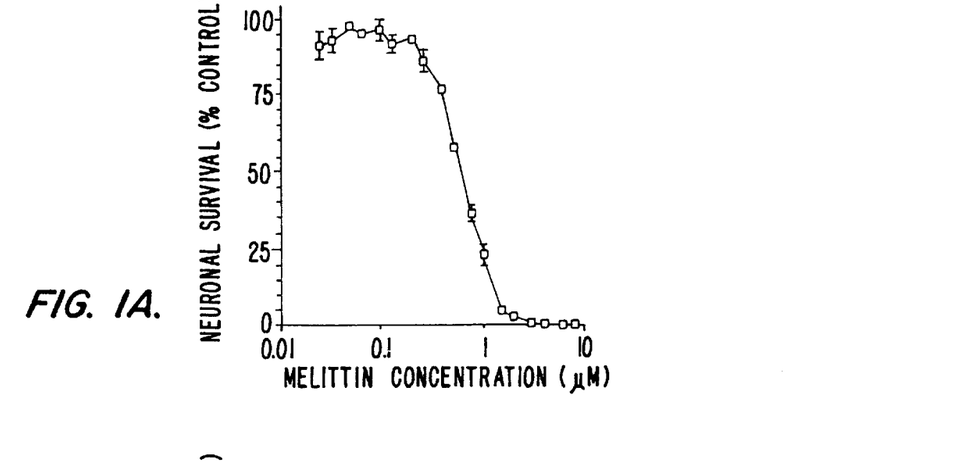
FIGS. 1A–1C show the effect of the PLA$_2$ inhibitor AN20579 on cortical neurons contacted with mellitin.
Figure 1B:
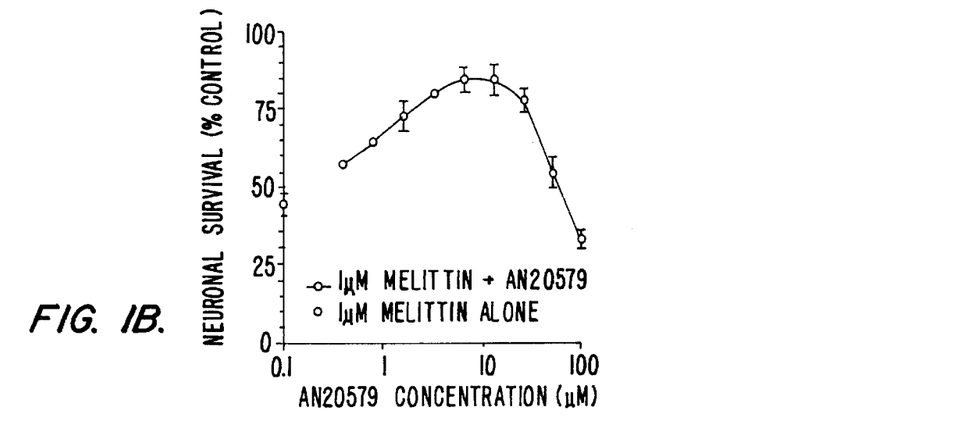
Figure 1C:
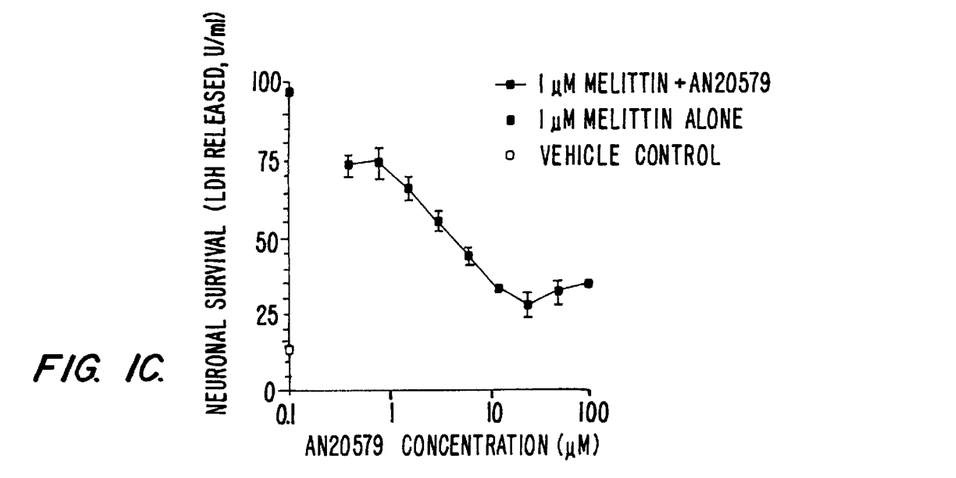

Melittin is a 26 amino acid peptide derived from bee venom and is an activator of $PLA_2$ (Shier, W. T. (1979) Proc. Natl. Acad. Sci. USA 76:195–199). We sought to determine if $PLA_2$ activation was toxic to rat cortical neurons and if this toxicity was inhibited by arachidonyl trifluoromethyl ketone, a $PLA_2$ inhibitor that is selective for calcium-dependent and calcium-independent cytosolic $PLA_2$s (Street et al. (1993), Biochemistry 32:5936–5940; Ackermann et al. (1995), J. of Biol. Chem. 270:445–450). (A) Melittin at a concentrations between 0.1 and 10 µM is toxic to rat cortical neurons over a 4 hour time period. (B) Arachidonyl trifluoromethyl ketone inhibits melittin toxicity as measured by alamarBlue. (C) Arachidonyl trifluoromethyl ketone inhibits melittin toxicity as measured by the release of the cytoplasmic enzyme LDH, a widely used measurement of neurodegeneration in cultured cortical neurons (Koh and Choi (1987), J. Neurosci. Methods 20:83). FIG. 1 shows the effect of the $PLA_2$ inhibitor AN20579 on cortical neurons contacted with mellitin.

Example 2: Serum Withdrawal Apoptosis

Figure 2:
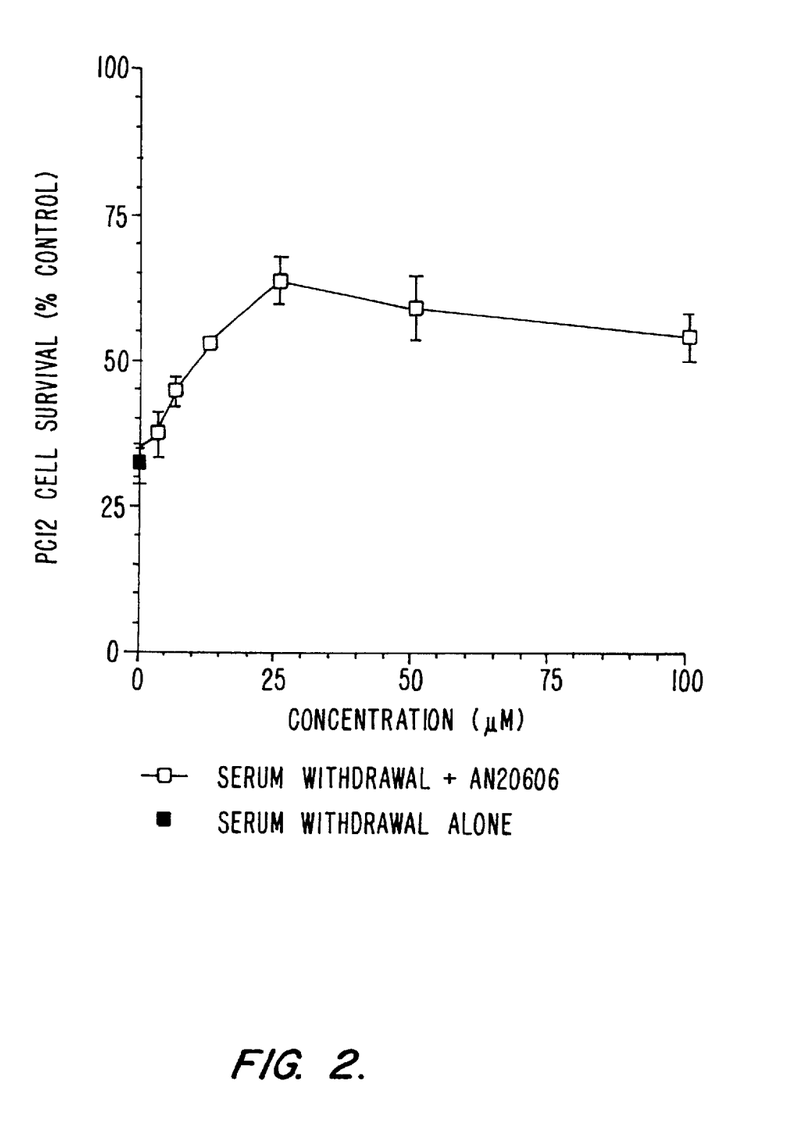
FIG. 2 shows the effect of the PLA$_2$ inhibitor AN20606 on PC12 neuronal cells induced to undergo apoptosis by serum withdrawal.
Figure 3A:
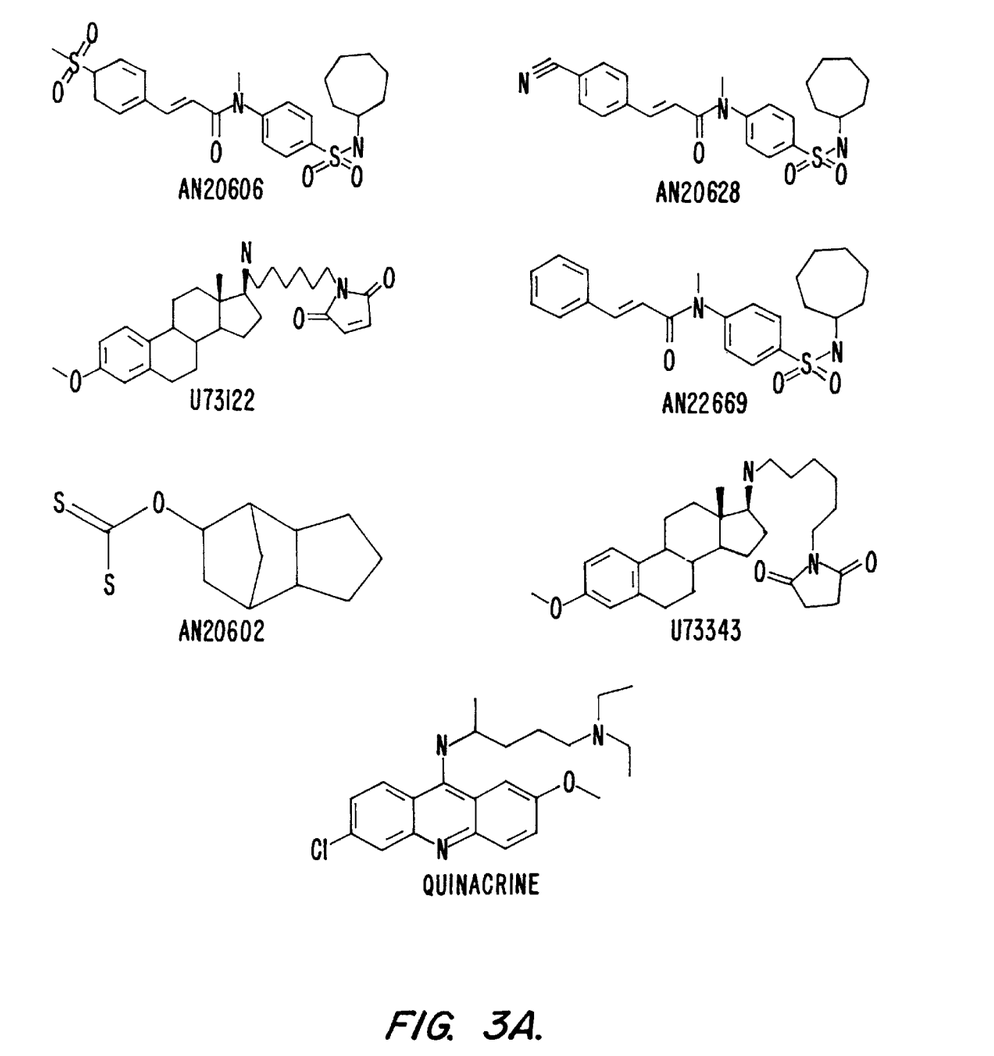
FIGS. 3A to 3M show the structural formulae of various exemplary compounds inhibiting PLA$_2$.
Figure 3B:
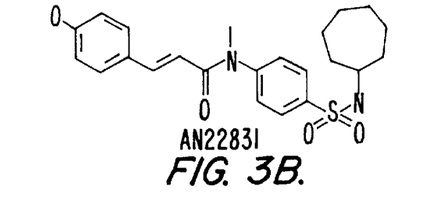
Figure 3C:
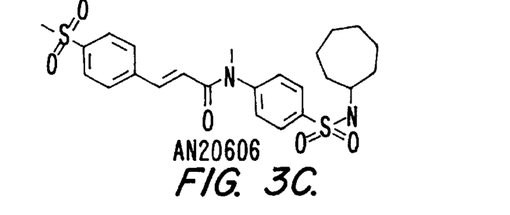
Figure 3D:
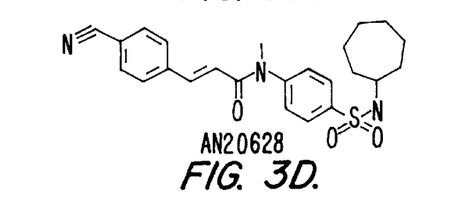
Figure 3E:
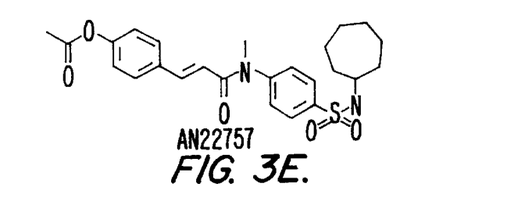
Figure 3F:
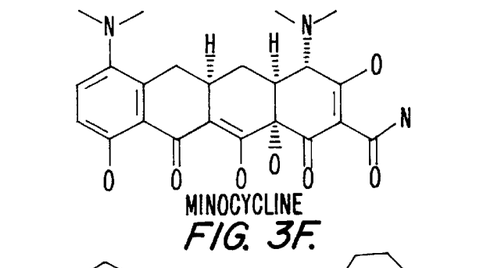
Figure 3G:
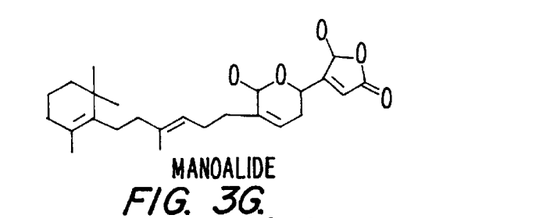
Figure 3H:
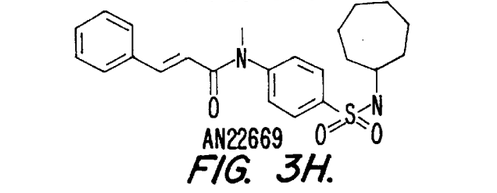
Figure 3I:
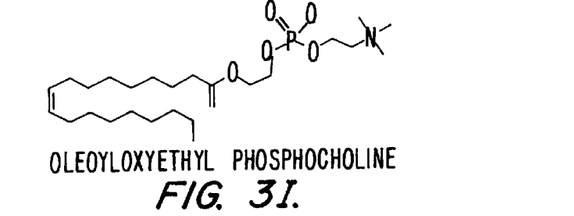
Figure 3J:
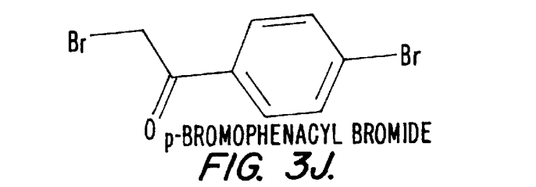
Figure 3K:
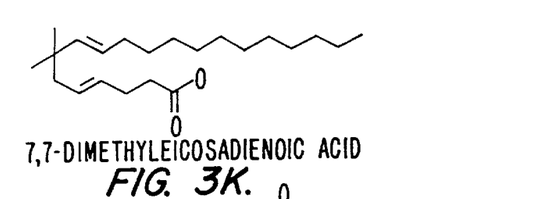
Figure 3L:
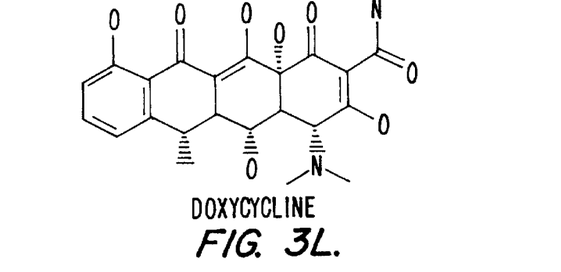
Figure 3M:
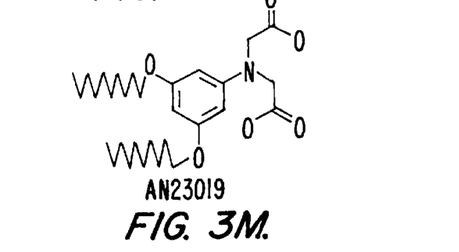

Serum withdrawal from cultured PC12 cells is model system used to study neuronal apoptosis and the ability of neurotrophic factors and other agents to inhibit this form of neurodegeneration (Rukenstein et al. (1991), J. Neurosci. 11:2552–2563). Cultured PC12 cells were plated in the absence of serum and various concentrations of an inhibitor of $PLA_2$ (AN20606) (Compound 25 in Oinuma et al. (1991) J. Med. Chem. 34:2260–2267). Cell survival was determined 1 day later using the alamarBlue assay™ and was compared to sister cultures maintained in serum-containing medium. Treatment with 25 µM AN20606 resulted in 46% inhibition of cell death. FIG. 2 shows the effect of the $PLA_2$ inhibitor AN20606 on PC12 neuronal cells induced to undergo apoptosis by serum withdrawal.

Example 3: NGF Deprivation-Induced Apoptosis

Sympathetic neurons in culture die by apoptosis when deprived of NGF (Martin et al. (1988), J. Cell Biol. 106:829–844). Rat sympathetic neurons were deprived of NGF in the presence of 20 µM AN20579, AN20606, or AN20628. Neuronal viability was assessed 24–30 hours later by their appearance and using phase-contrast light microscopy and compared to neurons maintained in the presence of 100 ng/ml NGF. Neurons maintained in the presence of NGF had a soma that was smooth and round to oval in shape, and possessed neurites with a relative uniform diameter and smooth appearance. Neurons deprived of NGF were characterized by neurite fragmentation, a shrunken and collapsed soma, and cell lysis. Neurons deprived of NGF in the presence of 20 µM AN20606 had intact neurites and a smooth soma. Neurons deprived of NGF in the presence of 20 µM AN20628 had intact neurites, a smooth to shrunken soma, but little evidence of cell lysis. Neurons deprived of NGF in the presence of 20 µM AN20579 showed signs of neurite fragmentation and cell lysis, but contained significantly more intact neurites and cell bodies than neurons deprived of NGF alone. AN20628=Compound 23 in Oinuma et al. (1991), J. Med. Chem. 34:2260-2267: N-cyclohepyl-4-[N-methyl-N[(E)-3-(4cyanophenyl-2-propenoyl]amino] benzenesulfonamide (AN 20628).

Summary of Experimental Examples

The Experimental Examples are indicative that agents which selectively inhibit $PLA_2$ activity protect human or rat neurons from toxicity resulting from exposure to apoptotic stimuli.

Although the present invention has been described in some detail by way of illustration for purposes of clarity of understanding, it will be apparent that certain changes and modifications may be practiced within the scope of the claims.

We claim:

1. A method for identifying active agents which inhibit neuronal degeneration, comprising administering an agent to a cell population consisting essentially of neurons or cells from neuronal cell lines, wherein said cell population is exposed to an apoptotic stimulus that induces an apoptotis-related neurodegenerative disease other than exposure to a product of the APP gene or a fragment thereof, the apoptotic stimulus producing neuronal degeneration in the cell population in the absence of the agent;

determining whether the presence of the agent produces a detectable reduction in the amount and/or rate of neuronal degeneration in the cell population; and determining whether the agent inhibits $PLA_2$ activity;

whereby production of a detectable reduction and inhibition of $PLA_2$ activity and inhibition of neuronal degeneration identifies the agent as an active agent.

2. The method according to claim 1, wherein the cell population consists essentially of neurons or cells from neuronal cell lines of human or rodent origin.

3. The method of claim 1, wherein the apoptotic stimulus is exposure to an amyloidogenic polypeptide which causes formation of extracellular deposits or intracellular inclusions.

4. A method for reducing or retarding neurodegeneration in a cell population consisting essentially of neurons or cells from neuronal cell lines exposed to an apoptotic stimulus other than exposure to a product of the APP gene or a fragment thereof, the apoptotic stimulus sufficient to produce neurodegeneration, comprising administering an efficacious dose of a $PLA_2$ inhibitor to retard or inhibit neuronal degeneration.

5. The method of claim 4, wherein the cell population consists essentially of cultured human or rodent cortical or hippocampal neurons.

6. The method of claim 4, wherein the apoptotic stimulus is mellitin, serum withdrawal, or growth factor deprivation.

7. The method of claim 1 wherein the apoptotic stimulus is reduction of a growth factor necessary for neuronal viability.

8. The method of claim 7 wherein the growth factor is NGF, BDNF or CTNF.

9. The method of claim 3 wherein the amyloidogenic polypeptide is prion protein or cystatin C.

10. The method of claim 4 wherein the apoptotic stimulus is exposure to an amyloidogenic polypeptide which causes formation of extracellular deposits or intracellular inclusions.

11. The method of claim 10 wherein the amyloidogenic polypeptide is prion protein or dystatin C.

12. The method of claim 1 wherein determining whether the agent inhibits $PLA_2$ activity comprises determining whether the agent inhibits cytoplasmic $PLA_2$ activity.

* * * * *